(12) United States Patent
Liao et al.

(10) Patent No.: US 10,294,100 B2
(45) Date of Patent: May 21, 2019

(54) METHOD FOR MANUFACTURING GAS DETECTOR BY MEMS PROCESS

(71) Applicant: TAIWAN CARBON NANO TECHNOLOGY CORPORATION, Miaoli County (TW)

(72) Inventors: Yu-Hsuan Liao, Miaoli County (TW); Fang-Song Tsai, Miaoli County (TW); Ya-Han Wu, Miaoli County (TW); Chun-Hsien Tsai, Miaoli County (TW); Ting-Chuan Lee, Miaoli County (TW); Chun-Jung Tsai, Miaoli County (TW)

(73) Assignee: Taiwan Carbon Nano Technology Corporation, Miaoli County (TW)

( * ) Notice: Subject to any disclaimer, the term of this patent is extended or adjusted under 35 U.S.C. 154(b) by 0 days.

(21) Appl. No.: 15/883,548

(22) Filed: Jan. 30, 2018

(65) Prior Publication Data

US 2019/0010048 A1 Jan. 10, 2019

(30) Foreign Application Priority Data

Jul. 7, 2017 (TW) .............................. 106122883 A
Sep. 21, 2017 (TW) .............................. 106132367 A

(51) Int. Cl.
*B81C 1/00* (2006.01)
*B81C 99/00* (2010.01)
*G01N 33/00* (2006.01)

(52) U.S. Cl.
CPC ........ *B81C 1/00825* (2013.01); *B81C 1/0088* (2013.01); *B81C 99/008* (2013.01); *G01N 33/0027* (2013.01); *B81B 2201/0214* (2013.01); *B81C 2203/031* (2013.01)

(58) Field of Classification Search
CPC . B81C 1/00825; B81C 99/008; B81C 1/0088; B81C 2203/031; G01N 33/0027; B81B 2201/0214
See application file for complete search history.

(56) References Cited

U.S. PATENT DOCUMENTS

| 9,249,008 | B2 | 2/2016 | Hsu et al. | |
| 2004/0075140 | A1* | 4/2004 | Baltes | G01N 27/12 257/347 |
| 2012/0138459 | A1* | 6/2012 | Chen | G01N 27/127 204/424 |

(Continued)

*Primary Examiner* — William F Kraig
*Assistant Examiner* — Vicki B. Booker
(74) *Attorney, Agent, or Firm* — Muncy, Geissler, Olds & Lowe, P.C.

(57) ABSTRACT

A method for manufacturing a gas detector by a micro-electrical-mechanical systems (MEMS) process. The method includes providing a MEMS wafer including a plurality of mutually adjacent units; forming a gas sensing material layer on the MEMS wafer; bonding a structure reinforcing layer and the MEMS wafer through anode bonding; providing an adhesive tape; performing a cutting process to form a gas detection unit; and adhering the gas detection unit on a substrate by the adhesive tape to form a gas detector. The structure reinforcing layer is capable of enhancing the strength of a device and preventing edge collapsing, and hence enhancing the overall yield rate and reducing costs.

6 Claims, 11 Drawing Sheets

(56) References Cited

U.S. PATENT DOCUMENTS

| | | | |
|---|---|---|---|
| 2013/0075255 A1* | 3/2013 | Moon | G01N 27/18 |
| | | | 204/427 |
| 2014/0262834 A1* | 9/2014 | Fix | G01N 27/4067 |
| | | | 205/784 |
| 2014/0339080 A1* | 11/2014 | Ochs | G01N 27/4141 |
| | | | 204/419 |
| 2015/0033827 A1* | 2/2015 | Burgi | G01N 27/04 |
| | | | 73/31.06 |
| 2017/0322173 A1* | 11/2017 | Widenmeyer | G01N 27/4071 |

* cited by examiner

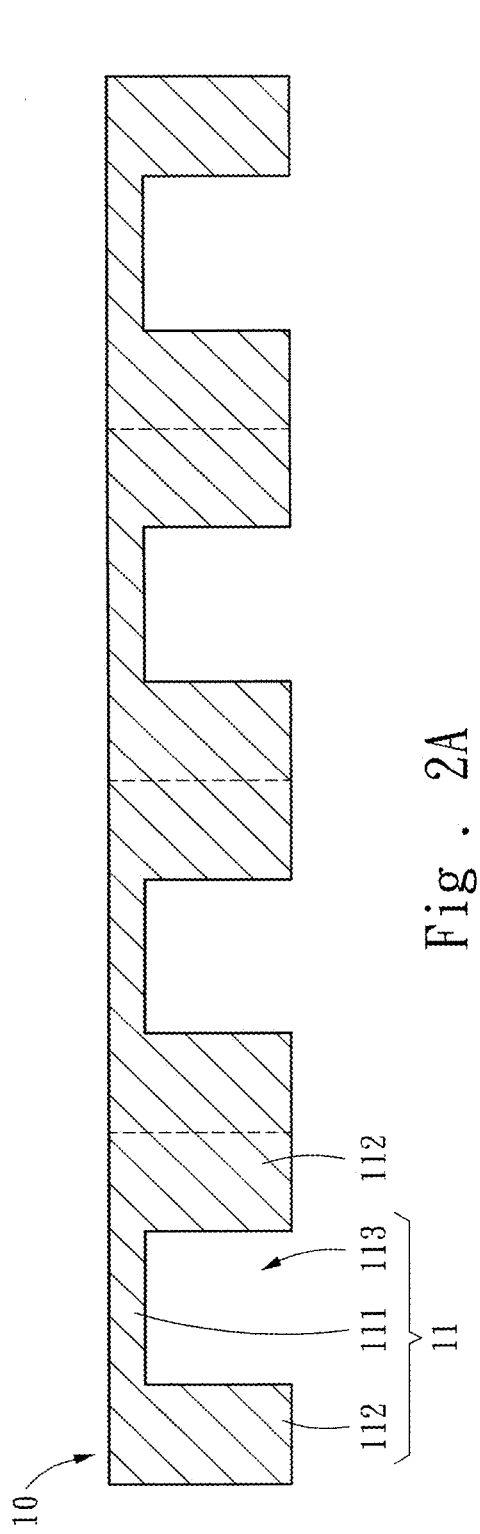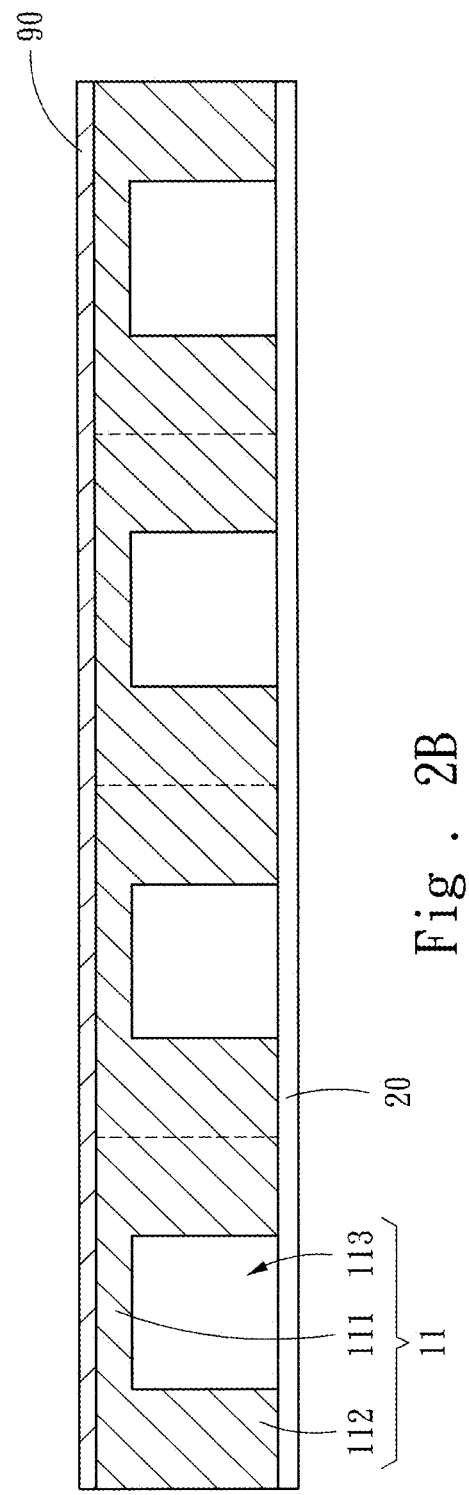

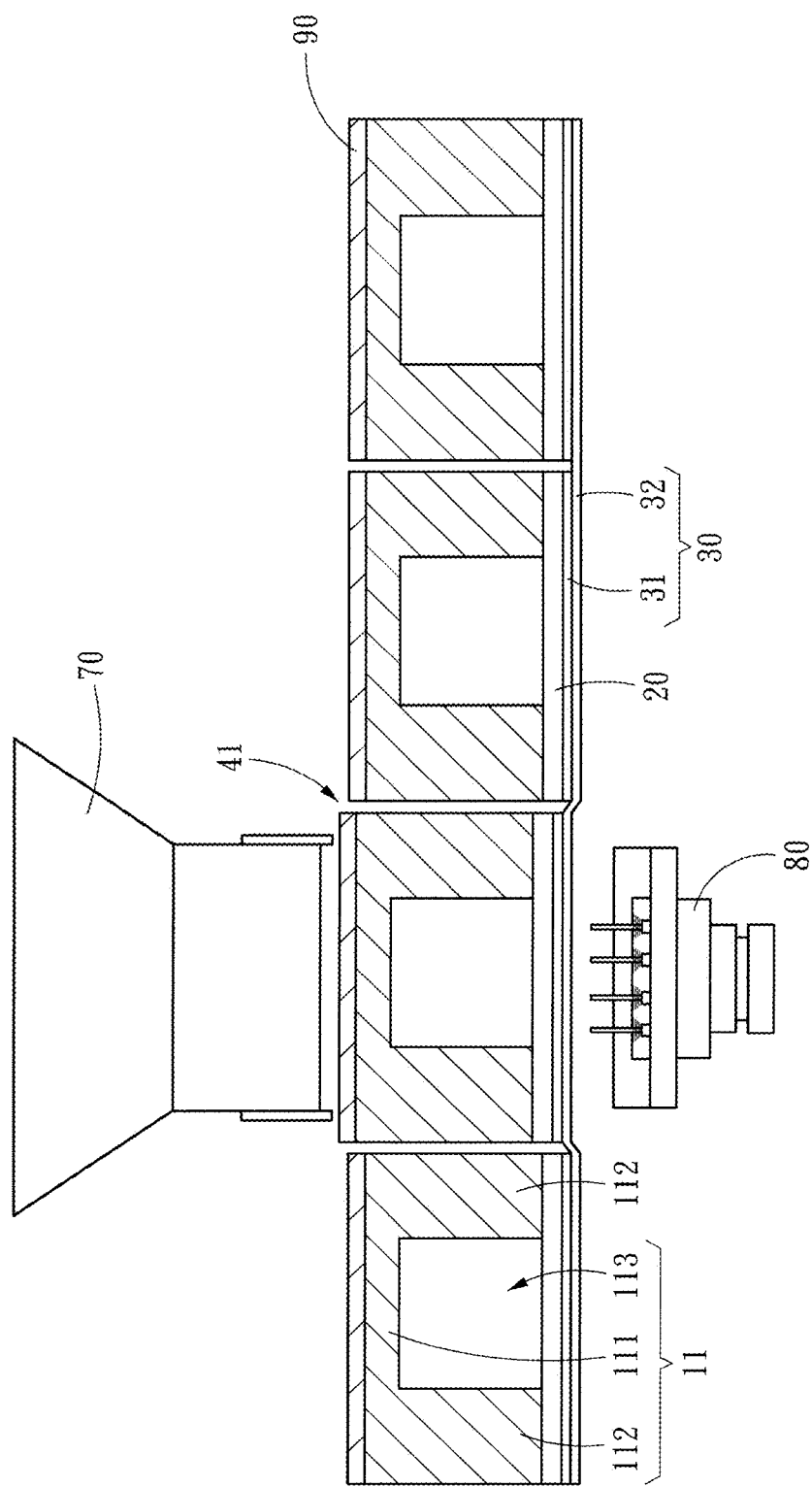

METHOD FOR MANUFACTURING GAS DETECTOR BY MEMS PROCESS

FIELD OF THE INVENTION

The present invention relates to a gas detector, and particularly to a method for manufacturing a gas detector by a micro-electrical-mechanical systems (MEMS) process.

BACKGROUND OF THE INVENTION

A micro-electro-mechanical system (MEMS) is a technique that incorporates microelectronics and machines and is a critical component for sensing or function execution. MEMS is extensively applied in daily tools such as accelerators, detectors and actuators, and has been developed towards miniaturization during the recent years. For example, the U.S. Pat. No. 9,249,008, "MEMS Device with Multiple Electrodes and Fabricating Method thereof", teaches a special arrangement of a first electrode, a second electrode and a third electrode, in a way that the MEMS device such as a differential pressure sensor, differential barometer, differential microphone and decoupling capacitor is facilitated to be miniaturized.

To effectively keep a heat source focused, a recess for accommodating air is usually designed in a common MEMS process. However, this recess reduces the strength of an overall device, and collapsing of an edge is easily caused during a subsequent cutting process, resulting in residuals or cleaning liquid likely accumulated during the cutting process, and hence a lowered yield rate and increased costs.

Further, to sense multiple types of gases, multiple MEMS sensors need to be installed by multiple repeated steps, which further increase production costs and prolong production time. Therefore, there is a need for a solution that resolves the above issues.

SUMMARY OF THE INVENTION

It is a primary object of the present invention to resolve issues of prior art, in which the strength of the overall device is reduced due to the recess provided, and collapsing of an edge is easily caused during a subsequent cutting process, resulting in residuals or cleaning liquid likely accumulated during the cutting process, and hence a lowered yield rate and increased costs.

It is another object of the present invention to resolve issues of prior art, in which steps need to be repeated for manufacturing a conventional micro-electro-mechanical systems (MEMS) multi-gas detector, increasing production costs and production time.

To achieve the above objects, the present invention provides a method for manufacturing a gas detector by a MEMS process. The method includes following steps.

In step S1, a MEMS wafer is provided, wherein the MEMS wafer includes a plurality of mutually adjacent units. Each of the plurality of units includes a top portion, a side block portion extending from an edge of the top portion, and a bottom chamber formed by the top portion and the side block portion in a surrounding manner. The side block portions of the plurality of units are mutually connected.

In step S2, a gas sensing material layer is formed on one side of the MEMS wafer opposing to the bottom chamber.

In step S3, a structure reinforcing layer is bonded with the MEMS wafer through anode bonding, wherein the structure reinforcing layer covers the bottom chambers.

In step S4, an adhesive tape is provided on one side of the structure reinforcing layer opposing to the MEMS wafer.

In step S5, a cutting process is performed along connecting positions of the side block portions of the plurality of units, and simultaneously on the structure reinforcing layer and the adhesive tape to form a plurality of gas detection units each comprising the bottom chamber.

In step S6, one of the plurality of gas detection units is adhered on a substrate by the adhesive tape to form a gas detector.

To achieve the above objects, the present invention further provides a method for manufacturing a multi-gas detector by a MEMS process. The method includes following steps.

In step P1, a MEMS wafer is provided. The MEMS wafer includes a plurality of mutually adjacent detection modules. Each of the plurality of detection modules includes a plurality of units, each of which includes a top portion, a side block portion extending from an edge of the top portion, and a bottom chamber formed by the top portion and the side block portion in a surrounding manner. The side block portions of the plurality of units are mutually connected.

In step P2, a gas sensing material layer is formed on one side of the MEMS wafer opposing to the bottom chamber. The gas sensing material layer includes a plurality of types of gas sensing materials formed on the different units.

In step P3, a structure reinforcing layer is bonded with the MEMS wafer through anode bonding, wherein structure reinforcing layer covers the bottom chambers.

In step P4, an adhesive tape is provided on one side of the structure reinforcing layer opposing to the MEMS wafer.

In step P5, a cutting process is performed along connecting positions of the plurality of detection modules, and simultaneously on the structure reinforcing layer and the adhesive tape to form a plurality of multi-gas detection units.

In step P6, one of the plurality of multi-gas detection units is adhered on a substrate by the adhesive tape to form a multi-gas detector.

In conclusion, the present invention provides following features.

1. The structure reinforcing layer enhances the overall strength, and prevents the issue of edge collapsing of the MEMS wafer during the cutting process, enhancing the yield rate and reducing costs.

2. The using of anode bonding alleviates damages on the MEMS wafer caused by heating, and high bonding levelness between the structure reinforcing layer and the MEMS wafer can be provided, without involving any adhesive or incurring an issue of obliqueness.

3. By forming the plurality of types of gas sensing materials on the different units, one of the plurality of multi-gas detection units including the plurality of types of gas sensing materials can be formed by one cutting process, reducing both production costs and production time.

BRIEF DESCRIPTION OF THE DRAWINGS

FIG. 2A to FIG. 2F are partial section views of a manufacturing process of a method according to the first embodiment of the present invention;

DETAILED DESCRIPTION OF THE PREFERRED EMBODIMENTS

Figure 1:
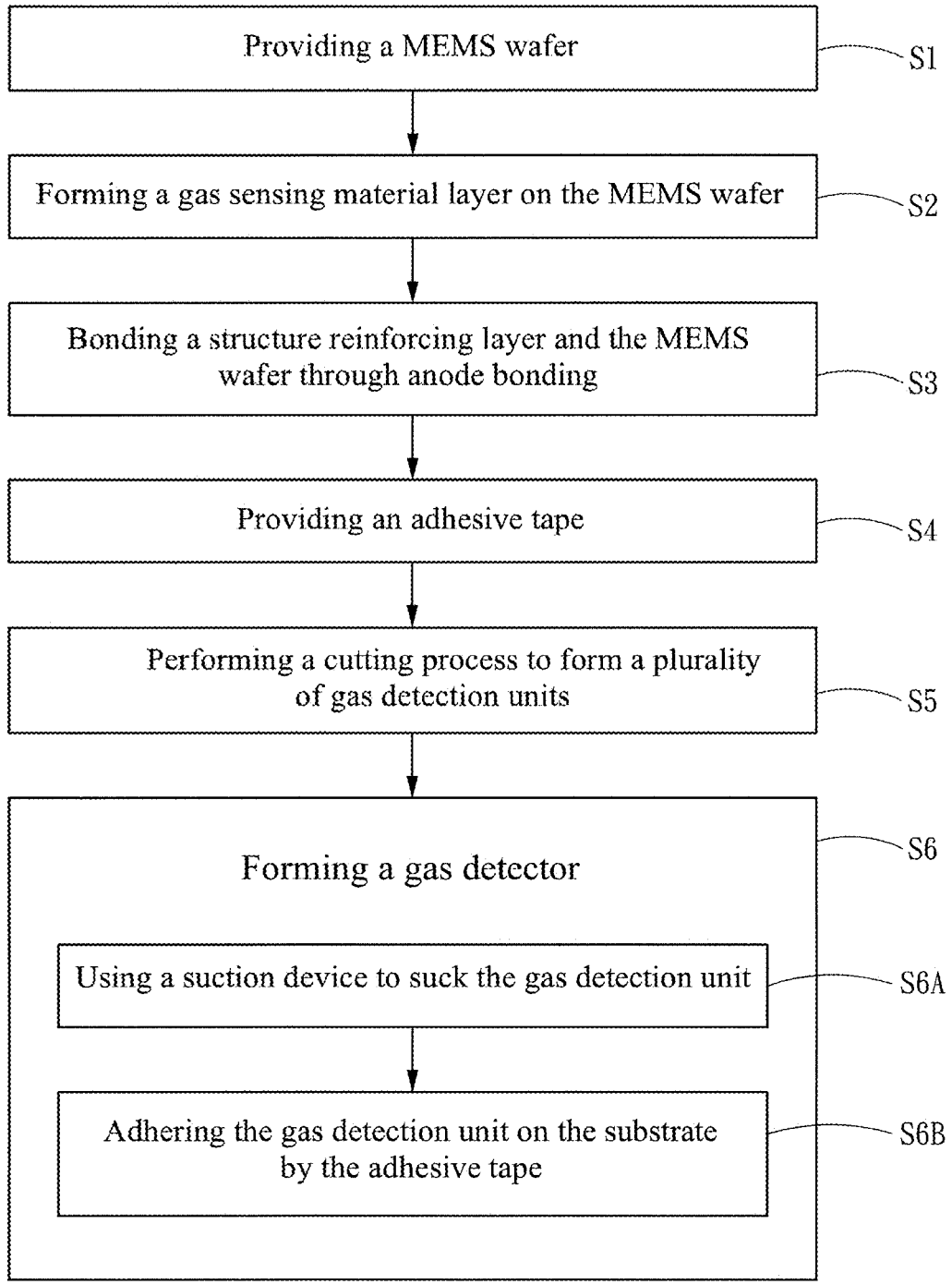
FIG. 1 is a flowchart of a method according to a first embodiment of the present invention.

FIG. 1 is a flowchart and FIG. 2A, FIG. 2B, FIG. 2C, FIG. 2D, FIG. 2E and FIG. 2F are partial section views of a manufacturing process of a method according to a first embodiment of the present invention. The method includes following steps.

In step S1, as shown in FIG. 2A, a micro-electro-mechanical systems (MEMS) wafer 10 is provided. The MEMS wafer 10 includes a plurality of mutually adjacent units 11. Each of the plurality of units 11 includes a top portion 111, a side block portion 112 and a bottom chamber 113. The side block portion 112 extends from an edge of the top portion 111, and the bottom chamber 113 is formed by the top portion 111 and the side block portion 112 in a surrounding manner. The plurality of units 11 are mutually connected via the side block portions 112 to form the MEMS wafer 10. In this embodiment, the MEMS wafer 10 is made of silicon, and the bottom chamber 113 is made through etching.

In step S2, as shown in FIG. 2B, a gas sensing material layer is formed on one side of the MEMS wafer 10 opposing to the bottom chamber 113.

In step S3, again referring to FIG. 2B, a structure reinforcing layer 20 is bonded with the MEMS wafer 10 through anode bonding, wherein the structure reinforcing layer 20 covers the bottom chambers 113. To reduce heat loss, in this embodiment, anode bonding is performed in a negative-pressure environment, thus reducing air in the bottom chamber 113 and effectively preventing air convection and heat transmission to keep a heat source focused. The structure reinforcing layer 20 is made of at least one of glass and borosilicate glass, and has a thickness between 0.2 mm and 1 mm. Anode bonding is capable of alleviating damages caused by heating upon the MEMS wafer 10, and requires no adhesive, achieving high bonding levelness between the structure reinforcing layer 20 and the MEMS wafer 10. In a preferred embodiment of the present invention, the structure reinforcing layer 20 is made of BOROFLOAT 33 (BF33) glass, and the MEMS wafer 10 is made of silicon.

Figure 2C:
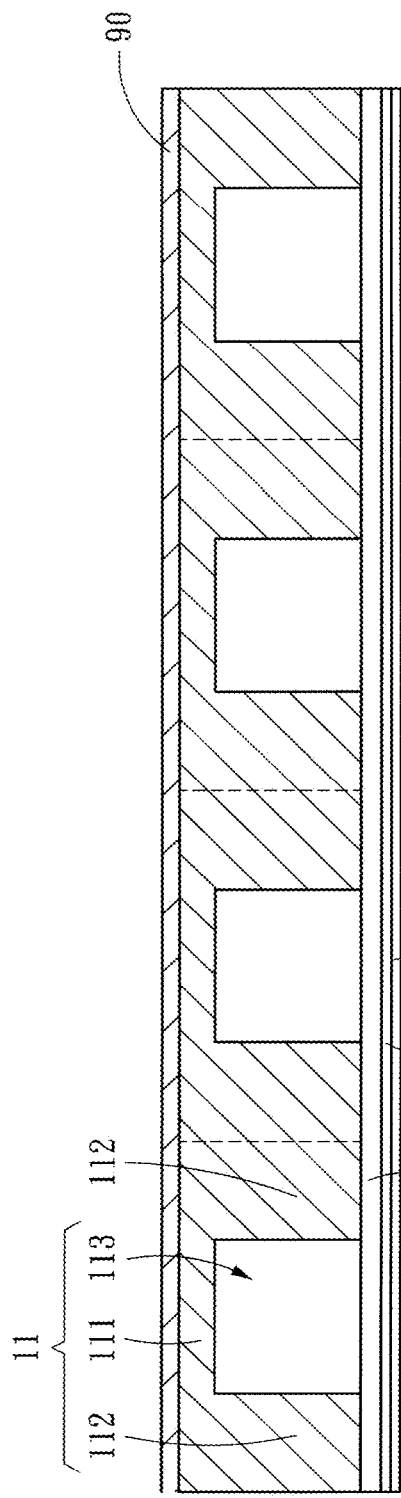

In step S4, as shown in FIG. 2C, an adhesive tape 30 is provided on one side of the structure reinforcing layer 20 opposing to the MEMS wafer 10. The adhesive tape 30 may be a die attach film (DAF) tape or a dicing tape. Further, the adhesive tape 30 may further include an adhesion layer 31 adjacent to the structure reinforcing layer 20, and a protection layer 32 opposing to the structure reinforcing layer 20. The protection layer 32 is for protecting the adhesiveness of the adhesion layer 31 and preventing dust from attaching thereon.

Figure 2D:
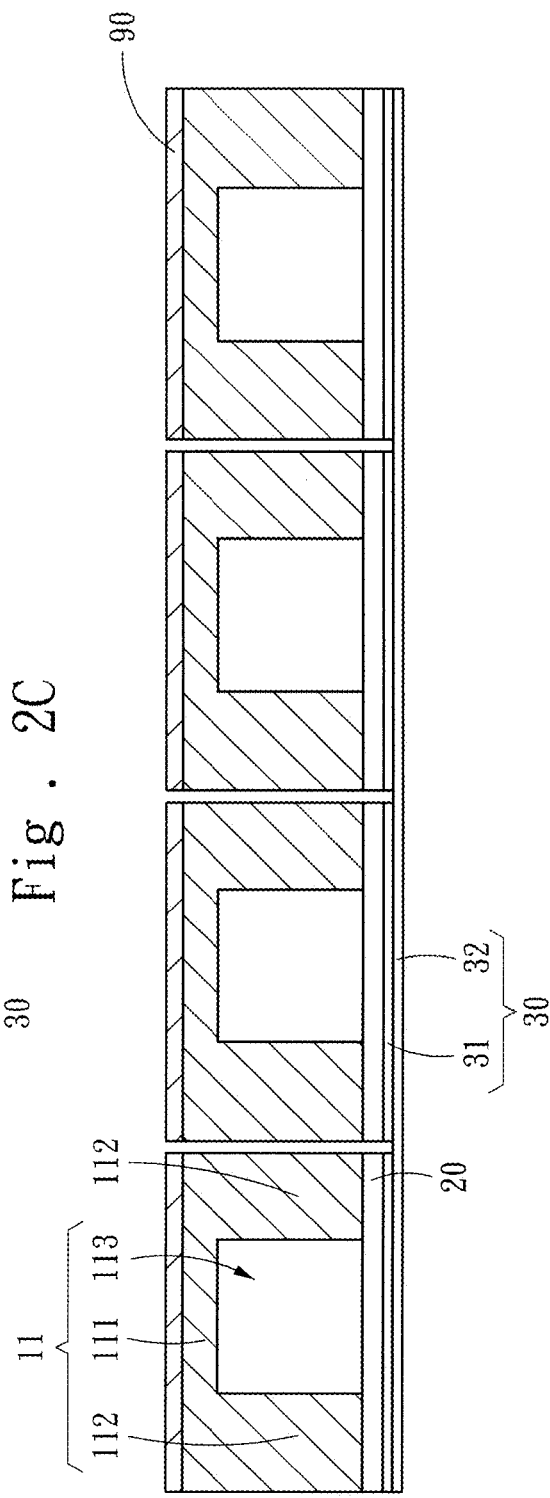

In step S5, as shown in FIG. 2D, a cutting process is performed along connecting positions of the side block portions 112 of the units 11, and simultaneously on the structure reinforcing layer 20 and the adhesive tape 30 to form a plurality of gas detection units 41. Each of the plurality of gas detection units 41 includes one bottom chamber 113. In this embodiment, the cutting process is performed through a laser (not shown) on the MEMS wafer 10, the structure reinforcing layer 20 and the adhesive tape 30. In an embodiment, the laser incidents from one side of the MEMS wafer 10 away from the structure reinforcing layer 20 to perform the cutting process. By replacing a conventional processing method with the laser, neither static electricity nor shearing effect is produced, thus preventing damages as well as possible residual internal stress of the MEMS wafer 10 and the structure reinforcing layer 20. The laser is capable of instantaneously completing the cutting process, involves an extremely small thermal affected area, and ensures high precision processing. Further, no cooling liquid is needed for laser processing, such that cleaning issues and pollution caused by waste materials can be reduced. With the structure reinforcing layer 20 provided, the strength of the overall device is enhanced, preventing edge collapsing during the cutting process and enhancing the yield rate as well as reducing costs.

Further, the adhesive tape 30 is capable of reliably binding the structure reinforcing layer 20 to prevent the scattering of the structure reinforcing layer 20 after the cutting process. Further, the protection layer 32 of the adhesive tape 30 remains intact as the laser is system-controlled.

Figure 2F:
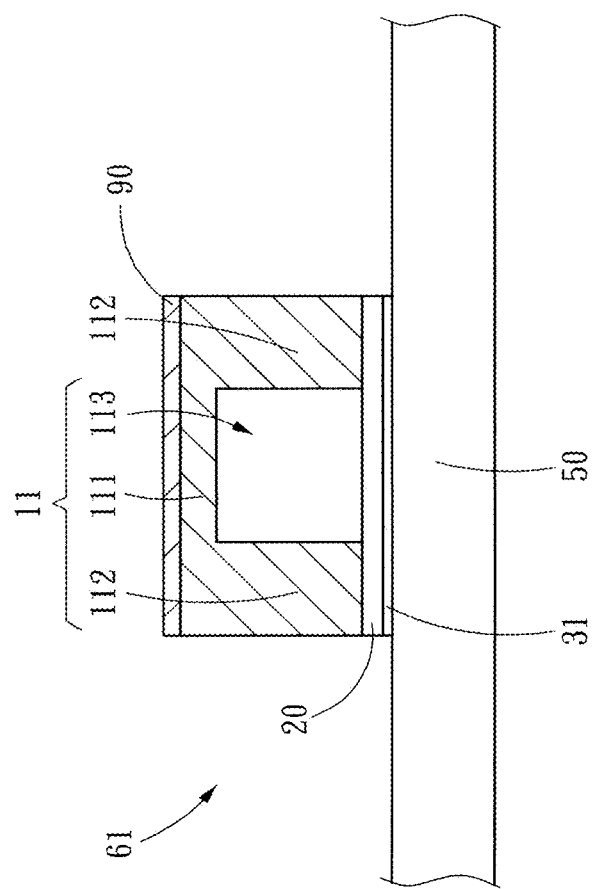

In step S6, as shown in FIG. 2E and FIG. 2F, one of the plurality of gas detection units 41 is adhered to a substrate 50 by the adhesive tape 30 to form a gas detector 61. Step S6 further includes following steps.

In step S6A, a suction device 70 is used to suck one of the plurality of gas detection units 41 from the side of the MEMS wafer 10. Meanwhile, a pushing device 80 is used to push the gas detection unit 41 from the side of the adhesive tape 30, so as to facilitate the suction device 70 to suck the gas detection unit 41 and to correspondingly move the gas detection unit 41 to the substrate 50.

In step S6B, the gas detection unit 41 is placed on the substrate 50, and is adhered to the substrate 50 via the adhesion layer 31 of the adhesive tape 30 to form the gas detector 61.

Figure 3:
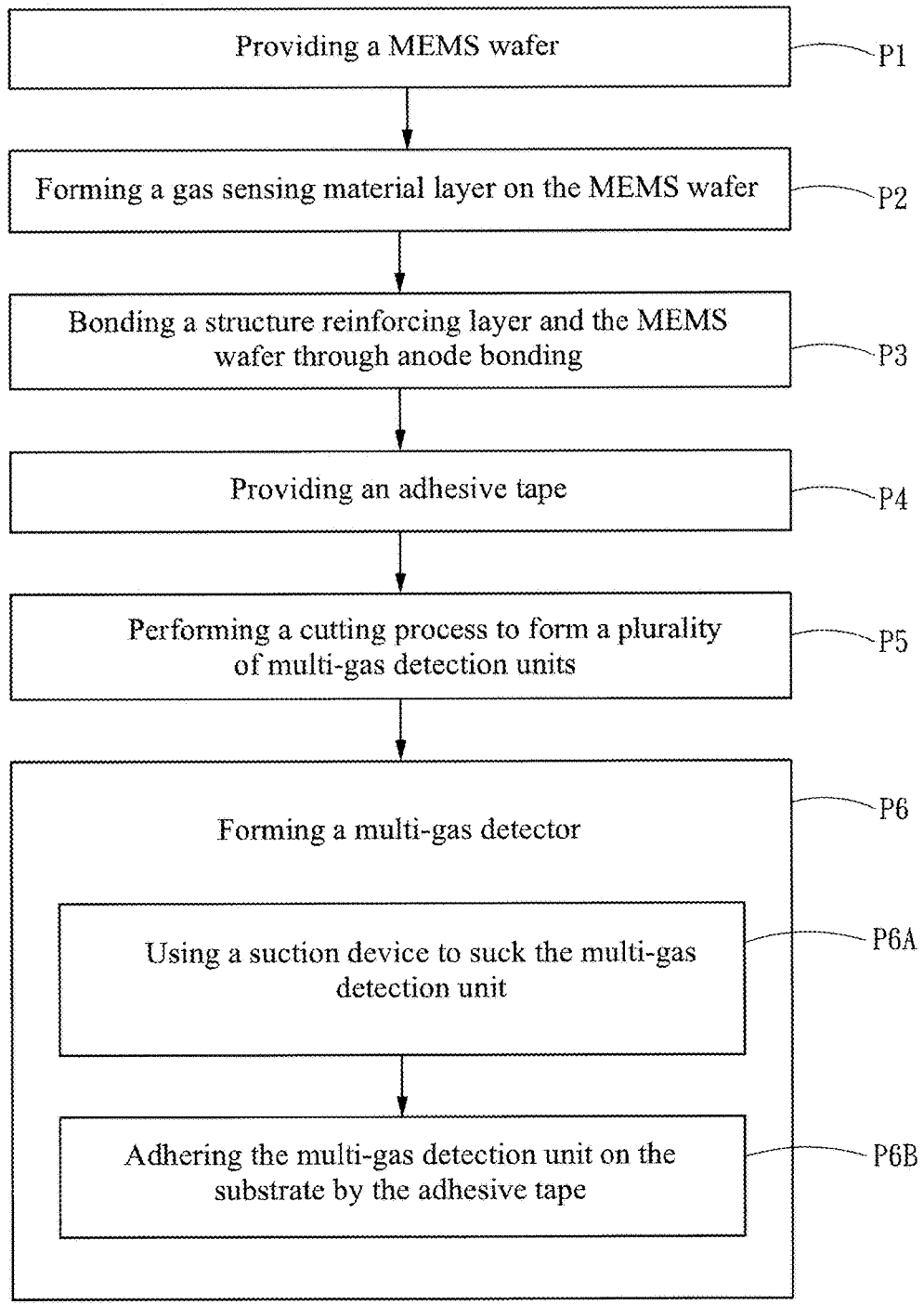
FIG. 3 is a flowchart of a method according to a second embodiment of the present invention.

FIG. 3 is a flowchart and FIG. 4A, FIG. 4B, FIG. 4C, FIG. 4D, FIG. 4E, FIG. 4F, and FIG. 4G are partial section views of a manufacturing process of a method according to a second embodiment of the present invention. The method includes following steps.

Figure 4A:
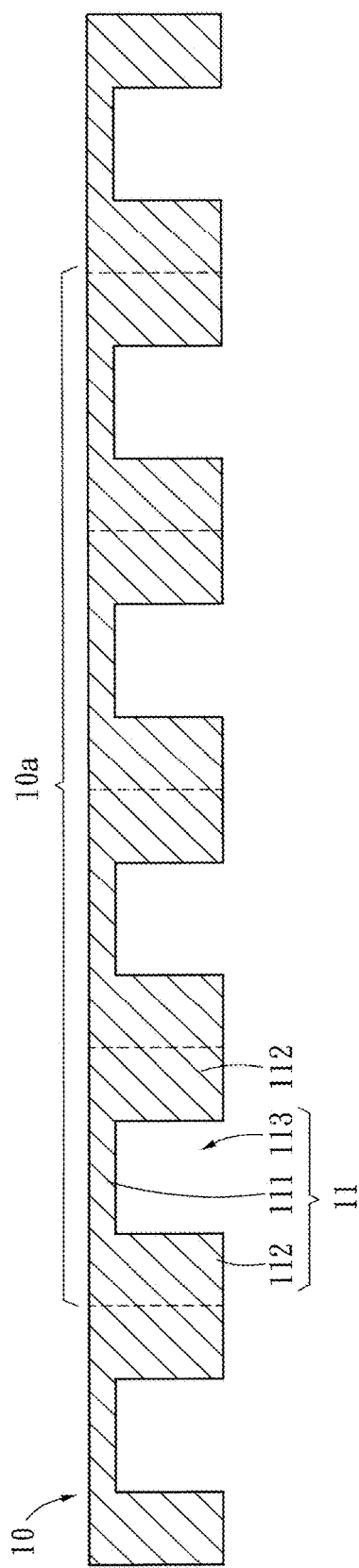
FIG. 4A to FIG. 4G are partial section views of a manufacturing process of a method according to the second embodiment of the present invention.

In step P1, referring to FIG. 4A, a MEMS wafer 10 is provided. The MEMS wafer 10 includes a plurality of mutually adjacent detection modules 10a each including a plurality of units 11. Each of the plurality of units 11 includes a top portion 111, a side block portion 112 and a bottom chamber 113. The side block portion 112 extends from an edge of the top portion 111, and the bottom chamber 113 is formed by the top portion 111 and the side block portion 112 in a surrounding manner. The side block portions 112 of the plurality of units 11 are mutually connected. In this embodiment, the MEMS wafer 10 is made of silicon, and the bottom chamber 113 is manufactured through etching.

Figure 4B:
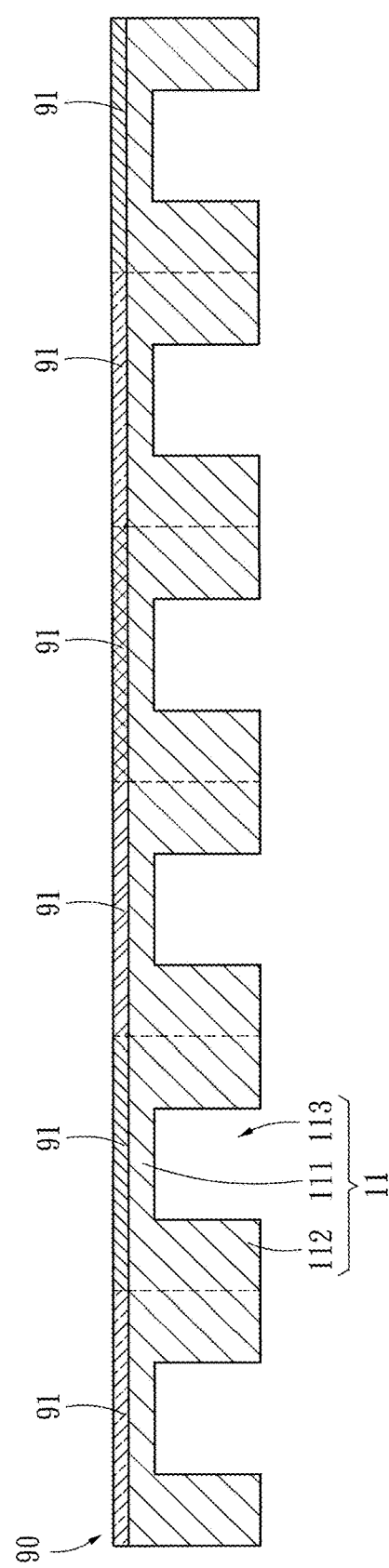

In step P2, referring to FIG. 4B, a gas sensing material layer 90 is formed on one side of the MEMS wafer 10 opposing to the bottom chamber 113. The gas sensing material layer 90 includes a plurality of types of gas sensing materials 91, which are respectively formed on different units 11 to sense different gases. In this embodiment, four different types of gas sensing materials 91 are given as an example.

Figure 4C:
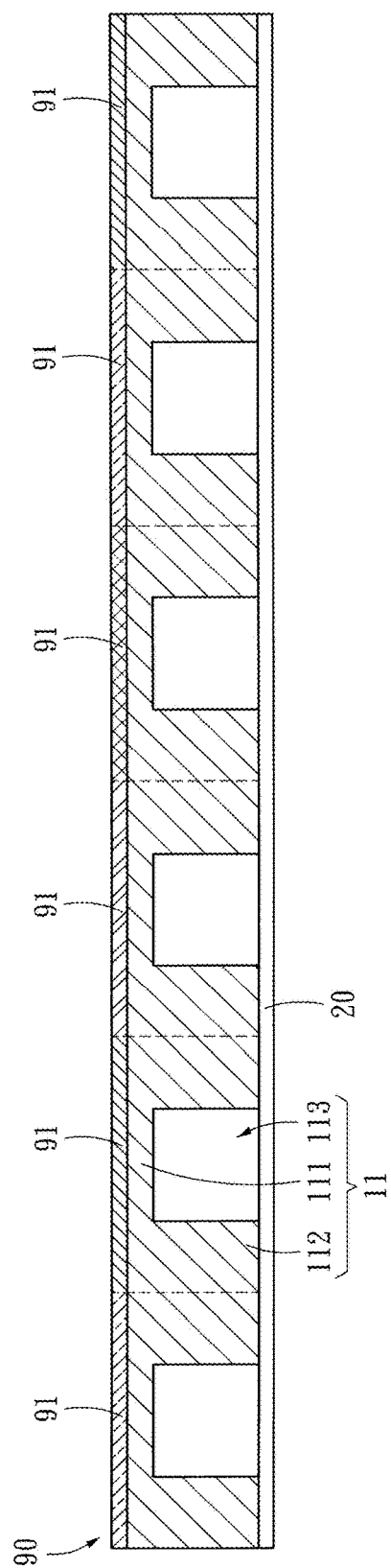

In step P3, referring to FIG. 4C, a structure reinforcing layer 20 and the MEMS wafer 10 are bonded through anode bonding. The structure reinforcing layer 20 covers the bottom chamber 113. The using of anode bonding alleviates damages caused by heating on the MEMS wafer 10, and provides high bonding levelness compared to conventional adhesives. Further, anode bonding performed in a negative-pressure environment reduces air in the bottom chamber 113, and effectively prevents air convection and heat transmission to keep a heat source focused. The structure reinforcing layer 20 may be made of at least one of glass and borosilicate glass, and has a thickness between 0.2 mm and 1 mm. In a preferred embodiment of the present invention, the structure reinforcing layer 20 is made of BF33 glass, and the MEMS wafer 10 is made of silicon.

Figure 4D:
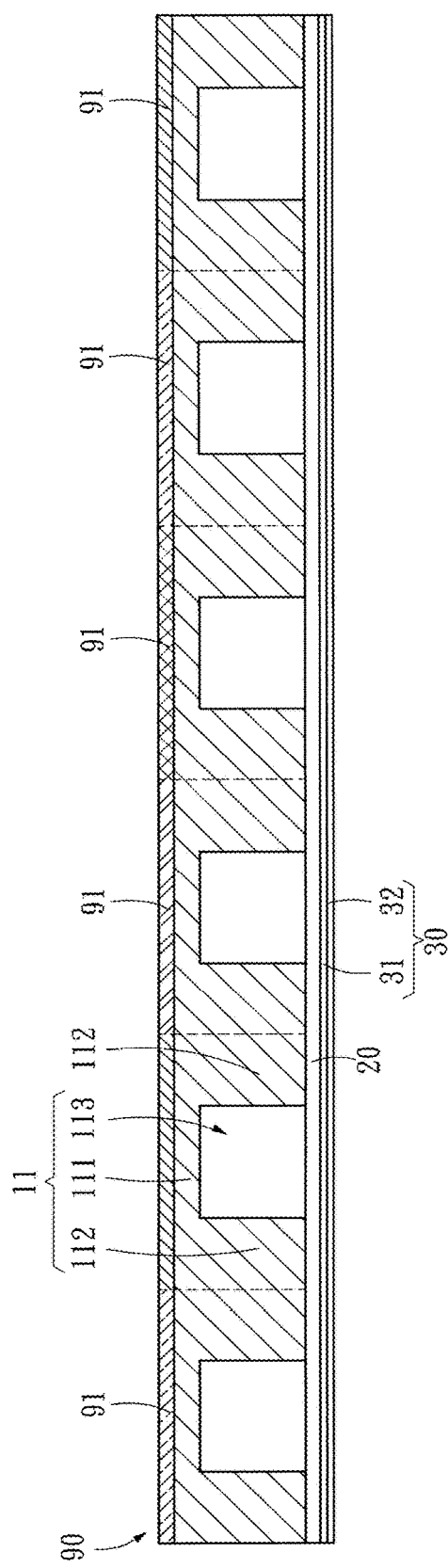

In step P4, referring to FIG. 4D, an adhesive tape 30 is provided on one side of the structure reinforcing layer 20 opposing to the MEMS wafer 10. The adhesive tape 30 may be a die attach film (DAF) tape or a dicing tape. Further, the adhesive tape 30 may further include an adhesion layer 31 adjacent to the structure reinforcing layer 20, and a protection layer 32 opposing to the structure reinforcing layer 20. The protection layer 32 is for protecting the adhesiveness of the adhesion layer 31.

Figure 4E:
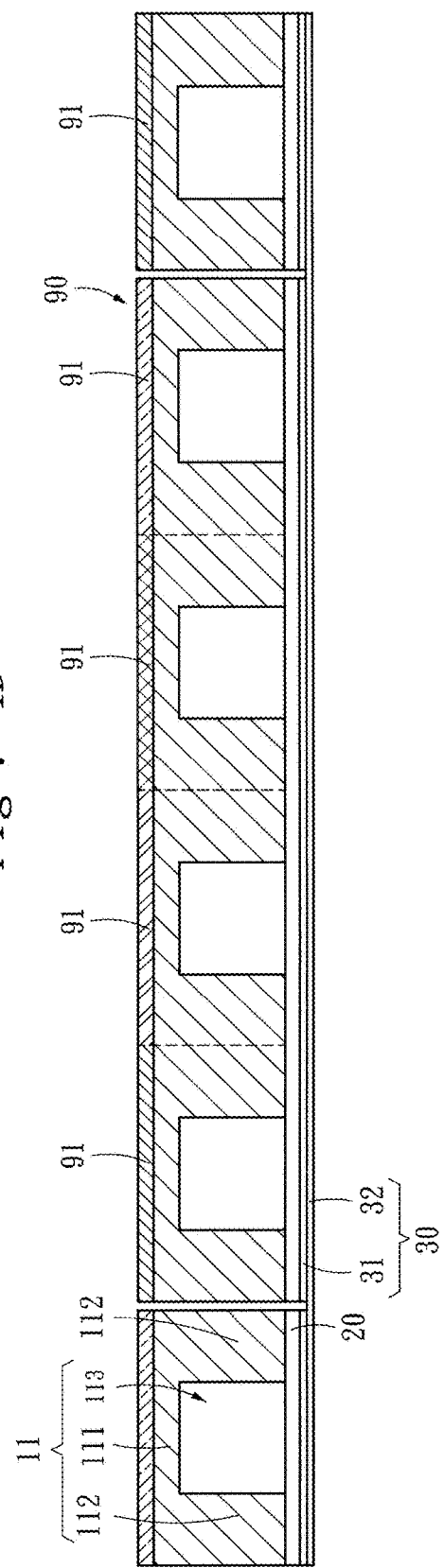

In step P5, referring to FIG. 4E, a cutting process is performed along connecting positions of the plurality of detection modules 10a, and simultaneously on the structure reinforcing layer 20 and the adhesive tape 30 to form a plurality of multi-gas detection units 42. With the structure reinforcing layer 20 provided, the strength of the overall device is enhanced, preventing edge collapsing during the cutting process and enhancing the yield rate as well as reducing costs. Because the plurality of units 11 of each of the plurality of detection modules 10a are provided with the different types of gas sensing materials 91, the plurality of multi-gas detection units 42 each including the plurality of types of gas sensing materials 91 can be obtained by one cutting process. Compared to a manufacturing process in which a single MEMS wafer 10 provided with only a single gas sensing material 91 needs to be provided in a plural quantity and then combined, the present invention reduces production costs as well as production time, and at the same time reduces the inventory of wafers.

In this embodiment, the cutting process is performed through laser (not shown) on the MEMS wafer 10, the structure reinforcing layer 20 and the adhesive tape 30. In an embodiment, the laser incidents from one side of the MEMS wafer 10 away from the structure reinforcing layer 20 to perform the cutting process. Advantages of performing cutting through laser are previously described, and shall be omitted herein.

Further, the adhesive tape 30 is capable of reliably binding the structure reinforcing layer 20 to prevent the plurality of multi-gas detection units 42 from scattering after the cutting process. Further, the laser, through system control, does not cut off the protection layer 32 of the adhesive tape 30.

Figure 4F:
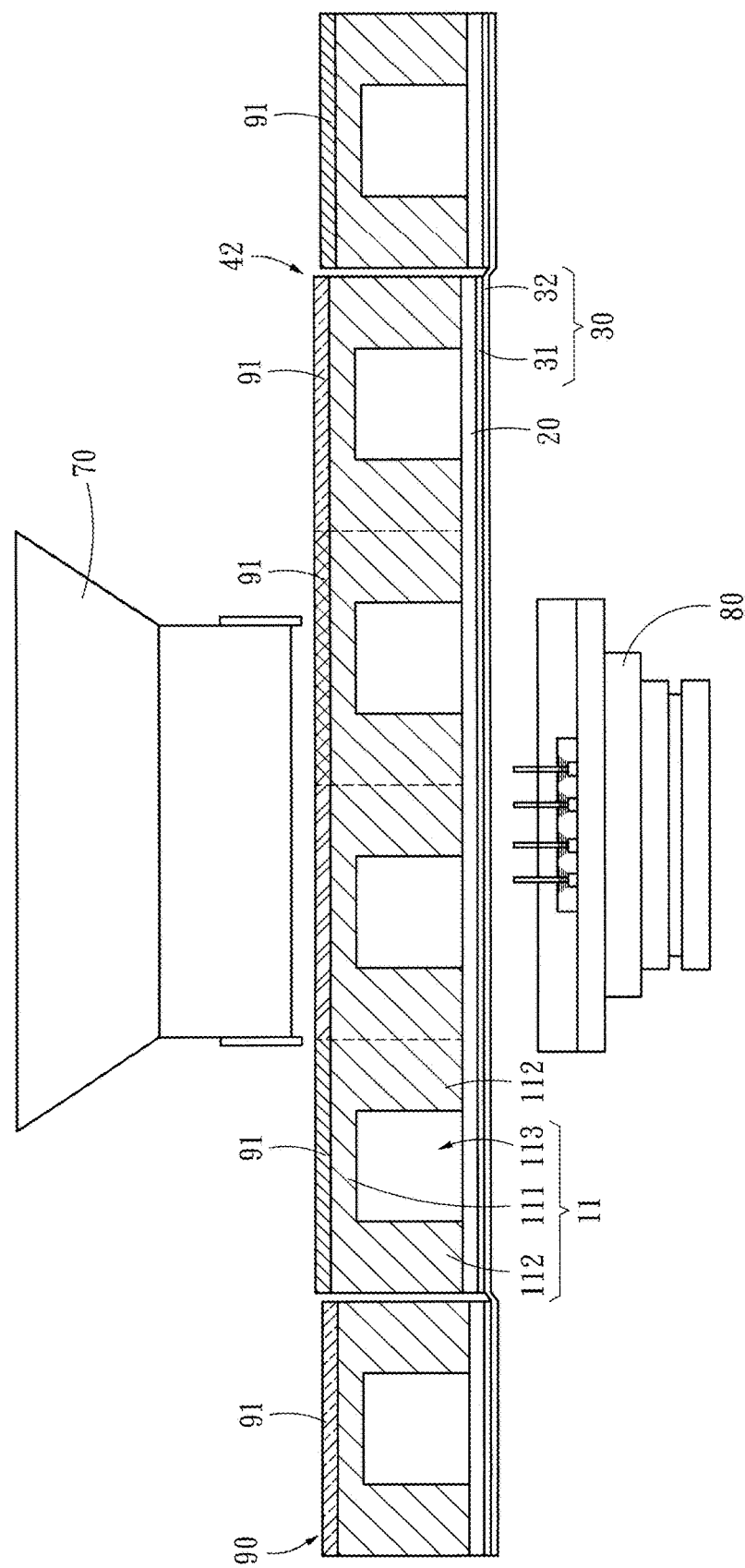
Figure 4G:
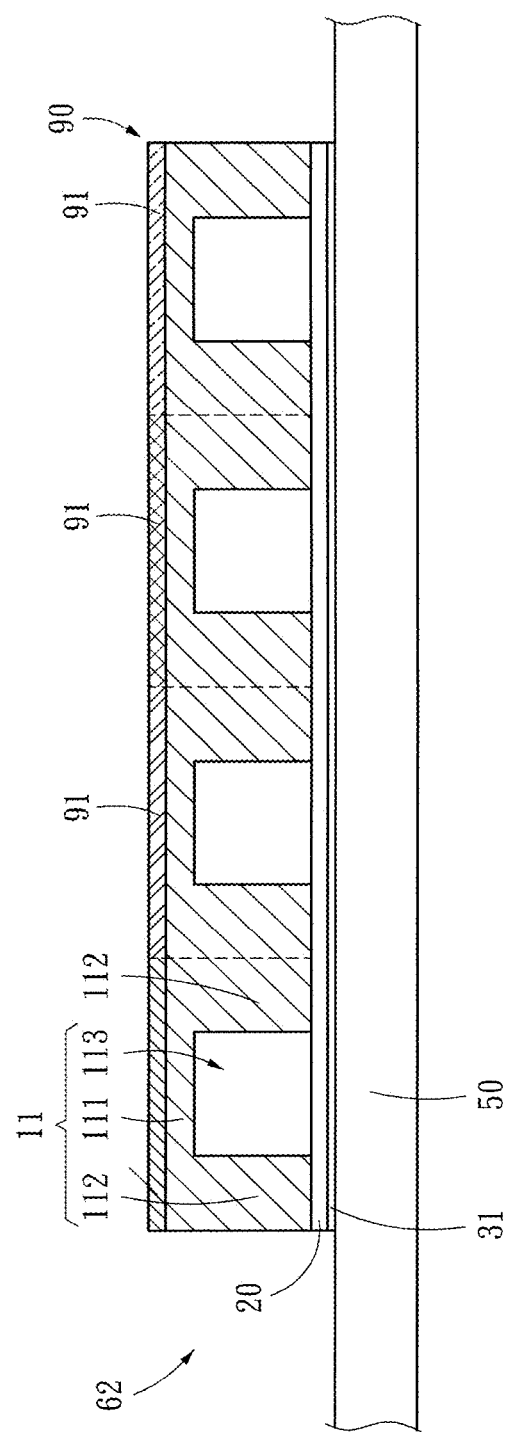

In step P6, referring to FIG. 4F and FIG. 4Q one of the plurality of multi-gas detection units 42 is adhered to a substrate 50 by the adhesive tape 30 to form a multi-gas detector 62. Because the plurality of units 11 of each of the plurality of detection modules 10a are mutually connected, adhesion precision is enhanced compared to a conventional solution of individually adhering the units 11. Step P6 further includes following steps.

In step P6A, a suction device 70 is used to suck one of the plurality of multi-gas detection units 42 from the side of the MEMS wafer 10. Meanwhile, a pushing device 80 is used to push the multi-gas detection unit 42 from the side of the adhesive tape 30, so as to facilitate the suction device 70 to suck the multi-gas detection unit 42 and to correspondingly move the multi-gas detection unit 42 to the substrate 50.

In step P6B, the multi-gas detection unit 42 is placed on the substrate 50, and is adhered via the adhesion layer 31 of the adhesive tape 30 to the substrate 50 to form the multi-gas detector 62. Using adhesive tape 30, issues of overfilling adhesive caused by a common liquid adhesive or obliqueness of the MEMS wafer 10 are eliminated.

What is claimed is:

1. A method for manufacturing a gas detector by a micro-electrical-mechanical systems (MEMS) process, comprising:
   S1: providing a MEMS wafer, the MEMS wafer comprising a plurality of mutually adjacent units, each of the plurality of units comprising a top portion, a side block portion extending from an edge of the top portion, and a bottom chamber formed by the top portion and the side block portion in a surrounding manner, the side block portions of the plurality of units mutually connected;
   S2: forming a gas sensing material layer on one side of the MEMS wafer opposing to the bottom chamber;
   S3: bonding a structure reinforcing layer with the MEMS wafer through anode bonding in a negative-pressure environment, wherein the structure reinforcing layer covers the bottom chambers, and is made of at least one selected from a group consisting of glass and borosilicate glass;
   S4: providing an adhesive tape on one side of the structure reinforcing layer opposing to the MEMS wafer;
   S5: performing a cutting process along connecting positions of the side block portions of the plurality of units to form a plurality of gas detection units each comprising the bottom chamber; and
   S6: adhering one of the plurality of gas detection units to a substrate by the adhesive tape to form a gas detector.

2. The method for manufacturing a gas detector by a MEMS process of claim 1, wherein a thickness of the structure reinforcing layer is between 0.2 mm and 1 mm.

3. The method for manufacturing a gas detector by a MEMS process of claim 1, wherein step S6 further comprises:
   S6A: using a suction device to suck one of the plurality of gas detection units from one side of the MEMS wafer and correspondingly moving the gas detection unit to the substrate; and
   S6B: adhering the gas detection unit on the substrate by the adhesive tape to form the gas detector.

4. A method for manufacturing a multi-gas detector by a micro-electrical-mechanical systems (MEMS) process, comprising:
   P1: providing a MEMS wafer, the MEMS wafer comprising a plurality of mutually adjacent detection modules, each of the plurality of detection modules comprising a plurality of units, each of the plurality of units comprising a top portion, a side block portion extending from an edge of the top portion, and a bottom chamber formed by the top portion and the side block portion in a surrounding manner, the side block portions of the plurality of units mutually connected;
   P2: forming a gas sensing material layer on one side of the MEMS wafer opposing to the bottom chamber, the gas sensing material layer comprising a plurality of types of gas sensing materials respectively formed on the plurality of units;
   P3: bonding a structure reinforcing layer with the MEMS wafer through anode bonding in a negative-pressure environment, wherein the structure reinforcing layer covers the bottom chambers, and is made of at least one selected from a group consisting of glass and borosilicate glass;
   P4: providing an adhesive tape on one side of the structure reinforcing layer opposing to the MEMS wafer;
   P5: performing a cutting process along connecting positions of the plurality of detection modules, and simultaneously on the structure reinforcing layer and the adhesive tape to form a plurality of multi-gas detection units; and P6: adhering one of the plurality of multi-gas detection units to a substrate by the adhesive tape to form a multi-gas detector.

5. The method for manufacturing a multi-gas detector by a MEMS process of claim 4, wherein a thickness of the structure reinforcing layer is between 0.2 mm and 1 mm.

6. The method for manufacturing a multi-gas detector by a MEMS process of claim 4, wherein step P6 further comprises:

P6A: using a suction device to suck one of the plurality of multi-gas detection units from one side of the MEMS wafer and correspondingly moving the multi-gas detection unit to the substrate; and P6B: adhering the multi-gas detection unit on the substrate by the adhesive tape to form the multi-gas detector.

* * * * *